United States Patent
Jahnke et al.

(10) Patent No.: US 10,654,023 B2
(45) Date of Patent: May 19, 2020

(54) SYSTEM AND METHOD FOR INCREASING A CARBON MONOXIDE CONTENT OF SYNGAS PRODUCED BY A STEAM METHANE REFORMER

(71) Applicant: FuelCell Energy, Inc., Danbury, CT (US)

(72) Inventors: Fred C. Jahnke, Rye, NY (US); Matthew Lambrech, Sherman, CT (US)

(73) Assignee: FUELCELL ENERGY, INC., Danbury, CT (US)

( * ) Notice: Subject to any disclaimer, the term of this patent is extended or adjusted under 35 U.S.C. 154(b) by 0 days.

(21) Appl. No.: 16/329,107

(22) PCT Filed: Aug. 29, 2017

(86) PCT No.: PCT/US2017/049161
§ 371 (c)(1),
(2) Date: Feb. 27, 2019

(87) PCT Pub. No.: WO2018/044913
PCT Pub. Date: Mar. 8, 2018

(65) Prior Publication Data
US 2019/0224641 A1    Jul. 25, 2019

Related U.S. Application Data

(60) Provisional application No. 62/381,375, filed on Aug. 30, 2016.

(51) Int. Cl.
*B01J 19/24* (2006.01)
*H01M 8/0612* (2016.01)
(Continued)

(52) U.S. Cl.
CPC ............. *B01J 19/245* (2013.01); *B01J 12/00* (2013.01); *C01B 3/38* (2013.01); *C07C 29/152* (2013.01);
(Continued)

(58) Field of Classification Search
CPC ...... C10G 2/32; B01J 19/245; C07C 29/1518; H01M 8/0618; H01M 8/0668
See application file for complete search history.

(56) References Cited

U.S. PATENT DOCUMENTS

2007/0099038 A1* 5/2007 Galloway .................. C10J 3/20
48/197 R
2010/0129691 A1   5/2010 Dooher et al.
(Continued)

FOREIGN PATENT DOCUMENTS

WO   WO-2007/122498 A2   11/2007

OTHER PUBLICATIONS

International Search Report and Written Opinion in PCT/US2017/049161 dated Nov. 23, 2017 (15 pages).

*Primary Examiner* — Lessanwork Seifu
(74) *Attorney, Agent, or Firm* — Foley & Lardner LLP

(57) ABSTRACT

A system for producing liquid fuel including a hydrocarbon source, a fuel cell unit configured to output anode exhaust gas containing a predetermined amount of $CO_2$, and a reformer configured to receive a first hydrocarbon feed portion from the hydrocarbon source and the anode exhaust gas from the fuel cell unit, such that the reformer is configured to output a syngas having a first $H_2/CO$ ratio of at most 2:1.

20 Claims, 5 Drawing Sheets

(51) Int. Cl.
    *C01B 3/38*      (2006.01)
    *B01J 12/00*     (2006.01)
    *C07C 29/152*    (2006.01)
    *H01M 8/14*      (2006.01)
    *H01M 8/124*     (2016.01)

(52) U.S. Cl.
    CPC ... *H01M 8/0618* (2013.01); *C01B 2203/0233* (2013.01); *C01B 2203/0283* (2013.01); *C01B 2203/061* (2013.01); *C01B 2203/062* (2013.01); *C01B 2203/066* (2013.01); *C01B 2203/1241* (2013.01); *C01B 2203/84* (2013.01); *H01M 2008/1293* (2013.01); *H01M 2008/147* (2013.01); *Y02E 60/526* (2013.01)

(56)            References Cited

U.S. PATENT DOCUMENTS

2013/0177824 A1    7/2013   Cui et al.
2014/0260311 A1    9/2014   Berlowitz et al.

* cited by examiner

SYSTEM AND METHOD FOR INCREASING A CARBON MONOXIDE CONTENT OF SYNGAS PRODUCED BY A STEAM METHANE REFORMER

CROSS-REFERENCE TO RELATED PATENT APPLICATION

This application is a U.S. National Stage of International Application No. PCT/US2017/049161 filed on Aug. 29, 2017, which claims the benefit of and priority to U.S. Provisional Patent Application No. 62/381,375 filed on Aug. 30, 2016, the entire disclosures of which are incorporated by reference herein.

BACKGROUND

The present disclosure relates to a steam methane reformer (SMR). In particular, the present disclosure relates to a system and method for increasing a carbon monoxide content of syngas produced by SMRs.

Steam methane reformers (SMRs) are generally used as a low-cost option to produce a syngas from a gas feedstock such as natural gas, refinery gas or biogas. The produced syngas can be further processed within the plant to yield various end products, including purified hydrogen, methanol, carbon monoxide and ammonia.

Agriculture operations, decomposition refuse within landfills, municipal water treatment plants, and food and beverage processors generate biomass that must be disposed of in an environmentally friendly and economical manner. Anaerobic digesters can reduce the scale of the biomass by a factor of ten, significantly reducing tipping or disposal fees; however, the digestion process and the decay of the biomass generates methane, or biogas, which may be considered to be an undesirable greenhouse gas. The biogas can be flared, but the flaring process generates pollutants such as nitric oxide ($NO_x$), which creates smog and wastes a potential fuel source. Capturing and using biogas as a fuel to generate liquid fuels solves these challenges in a carbon-neutral manner.

In the steam methane reforming process, high-temperature steam is used to produce syngas from a methane source, such as natural gas or biogas. See FIGS. 1A and 1B. In an endothermic reforming reaction, methane reacts with steam in the presence of a catalyst to produce hydrogen and carbon monoxide, according to the following formula (1):

$$CH_4 + H_2O \leftrightarrow CO + 3H_2 \qquad (1)$$

At the same time, a slightly exothermic water-gas shift reaction takes place in which the carbon monoxide and steam are reacted using a catalyst to produce carbon dioxide and more hydrogen, according to the following formula (2):

$$CO + H_2O \leftrightarrow CO_2 + H_2 \qquad (2)$$

The water-gas shift reaction may also be reversed to produce carbon monoxide from carbon dioxide and hydrogen. Syngas, or synthesis gas, is the fuel gas mixture comprised of hydrogen, carbon monoxide, and some carbon dioxide generated from these reactions.

An additional step of pressure-swing adsorption (PSA) may take place in which carbon dioxide and other impurities, such as unconverted methane and water, are removed from the gas stream, leaving essentially only hydrogen and carbon monoxide. This hydrogen and carbon monoxide can then be used to produce higher hydrocarbons such as methanol, other alcohols, or liquids from a Fischer-Tropsch (FT) reaction.

Steam reforming of gaseous hydrocarbons is seen as a potential way to provide hydrogen fuel for low temperature fuel cells. In this case, a lower temperature shift reactor is located between the reformer and the PSA to convert most of the CO from the reformer to $H_2$ and $CO_2$. Also, the CO is removed from the shifted syngas along with the $CO_2$ and other impurities to produce pure $H_2$.

Methanol can be synthesized from syngas according to the following formula (3):

$$CO + 2H_2 \leftrightarrow CH_3OH \qquad (3)$$

The reaction of formula (3) may be carried out in the presence of a catalyst, for example, a copper-based catalyst.

Carbon monoxide is preferred over carbon dioxide as a reactant for producing methanol. Therefore, it is desirable to produce syngas with a higher carbon monoxide content than is normally produced from the SMR, especially when methane is the feed gas. Also, a very low carbon dioxide content is desired, since $CO_2$ reacts with $H_2$ to produce $CO+H_2O$, and the $H_2O$ reduces the reaction rate and yield of desired products. For best results, the theoretically optimal stoichiometric number is 2.0 for converting syngas to methanol and other FT liquid compounds, as seen in formula (4) below:

$$SN = \frac{[H_2] - [CO_2]}{[CO] + [CO_2]} = 2.0 \qquad (4)$$

In other words, for methanol synthesis, it is desirable to have a 2:1 ratio of hydrogen to carbon monoxide without any $CO_2$.

Dimethyl ether (DME) can be synthesized by methanol dehydration according to the following formula (5):

$$2CH_3OH \leftrightarrow CH_3OCH_3 + H_2O \qquad (5)$$

The reaction of formula (5) may be carried out in the presence of a catalyst, for example, a silica-alumina catalyst. The catalyst used in the synthesis of DME is often different from the catalyst used in the synthesis of methanol. The advantage of DME is that it can be used as a direct substitute for diesel fuel in a diesel engine and produces fewer emissions than normal diesel fuel.

In conventional systems in which natural gas is converted to syngas, which is used to produce liquid fuel (see FIG. 1A), the hydrogen to carbon monoxide ratio will be higher (i.e. 6/1 $H_2/CO$) than desired due to the equilibrium composition for the reformed gas. For example, when natural gas from a pipeline is used as the SMR feed, the hydrogen to carbon monoxide ratio produced is much higher than the desired 2/1 ratio (see FIG. 1A). One method to increase CO production in an SMR is to add $CO_2$ to the hydrocarbon feed to the SMR. One way to do this is to use a feed with a high $CO_2$ content. In particular, in order to decrease the hydrogen to carbon monoxide ratio, some systems use biogas/anaerobic digester gas (ADG) as the SMR feed (se FIG. 1B), as opposed to natural gas from a pipeline. For example, the ADG may have a 60/40 methane to carbon dioxide composition. However, the limited biogas availability limits the potential production sites.

A need exists for improved technology, including technology related to a system and method for increasing a carbon monoxide content of syngas produced by steam methane reformers.

SUMMARY

In certain embodiments, a system for producing liquid fuel includes a hydrocarbon source, a fuel cell unit configured to output anode exhaust gas containing $CO_2$, and a reformer configured to receive a first hydrocarbon feed portion from the hydrocarbon source and the anode exhaust gas from the fuel cell unit, such that the reformer is configured to output a syngas having a first $H_2/CO$ ratio of at most 2:1.

In one aspect, the hydrocarbon source is natural gas from at least one of a production gas well or a pipeline or a biogas comprising a methane source.

In one aspect, the reformer is configured to operate at a temperature outside of the range of 30° C. to 250° C.

In one aspect, an anode of the fuel cell unit is configured to receive a second hydrocarbon feed portion from the hydrocarbon source.

In one aspect, the fuel cell unit is further configured to receive a first portion of $CO_2$ output by the reformer.

In one aspect, the system further includes an anode gas oxidizer combustor configured to receive a second portion of $CO_2$ output by the reformer, wherein a cathode of the fuel cell unit is configured to receive $CO_2$ output by the anode gas oxidizer combustor.

In one aspect, the syngas is converted to the liquid fuel comprising at least one of methanol or a Fischer-Tropsch liquid.

In one aspect, the fuel cell unit comprises a direct molten carbonate fuel cell (MCFC) configured to operate at a temperature in the range of 600° C. to 700° C.

In one aspect, the fuel cell unit comprises a solid oxide fuel cell (SOFC) configured to operate at a temperature in the range of 800° C. to 1000° C.

In one aspect, the liquid fuel is methanol, wherein the hydrocarbon source is a natural gas source, and wherein the reformer is a steam methane reformer configured to receive a natural gas feed from the natural gas source.

In one aspect, the reformer is configured to operate at a temperature outside of the range of 30° C. to 250° C.

In one aspect, the anode exhaust gas is added to the first hydrocarbon feed portion such that the reformer is configured to receive the first hydrocarbon feed portion and the anode exhaust gas as a single stream.

In one aspect, the MCFC is configured to output anode exhaust gas comprising ($H_2$+CO) at an amount in the range of 20% to 40% and $CO_2$ at an amount in the range of 60% to 80%, wherein the syngas is configured to receive the ($H_2$+CO) output from the anode exhaust gas, and wherein a cathode of the MCFC is configured to receive $CO_2$ from at least one of: $CO_2$ separated from the syngas, $CO_2$ output by an anode gas oxidizer combustor, or a $CO_2$-containing flue gas.

In one aspect, the SOFC is configured to output anode exhaust gas comprising ($H_2$+CO) at an amount in the range of 40% to 60% and $CO_2$ at an amount in the range of 40% to 60%, wherein the syngas is configured to receive the ($H_2$+CO) output from the anode exhaust gas, and wherein the reformer is further configured to receive recycled $CO_2$ separated from the syngas.

In one aspect, a self-contained electrical power generation system includes any one of the systems for producing liquid fuel disclosed herein.

One of ordinary skill in the art would appreciate that the aspects described above are not mutually exclusive and may be combined.

These and other advantageous features will become apparent to those reviewing the disclosure and drawings.

BRIEF DESCRIPTION OF THE DRAWINGS

In FIG. 3, M-BOP stands for mechanical balance of plant (i.e., fuel flow control, humidification, sulfur removal, and heating), and E-BOP stands for electrical balance of plant (i.e., the conversion of DC power from the fuel cell to AC power for export to a grid or use to power processing equipment).

DETAILED DESCRIPTION

Figure 1A:
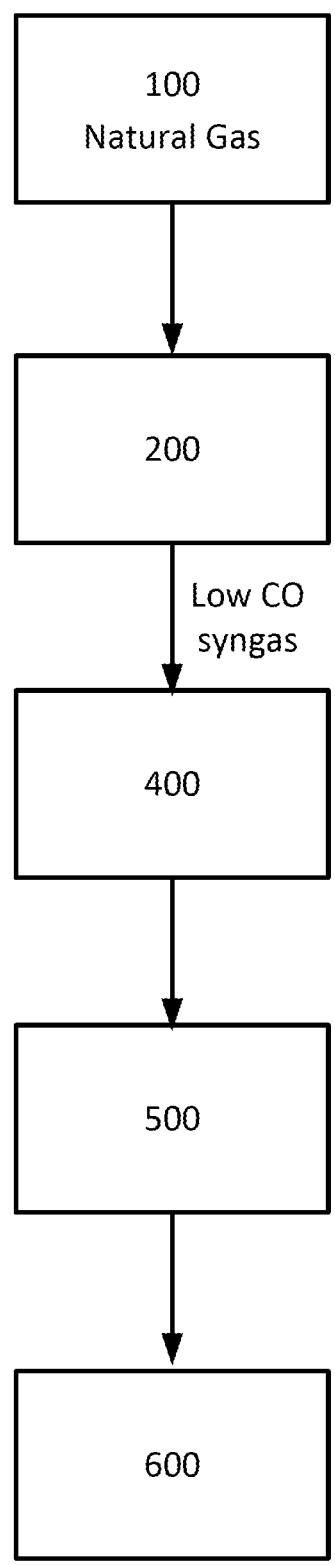
FIG. 1A is a schematic illustration of a conventional system that uses natural gas from a pipeline as a feed gas for a steam methane reformer.
Figure 1B:
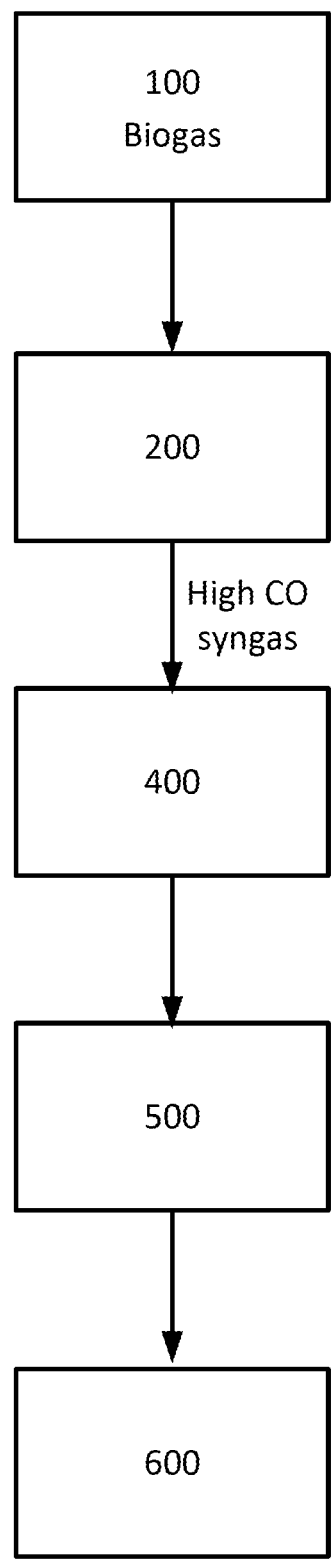
FIG. 1B is a schematic illustration of a conventional system that uses biogas as a feed gas for a steam methane reformer.
Figure 2:
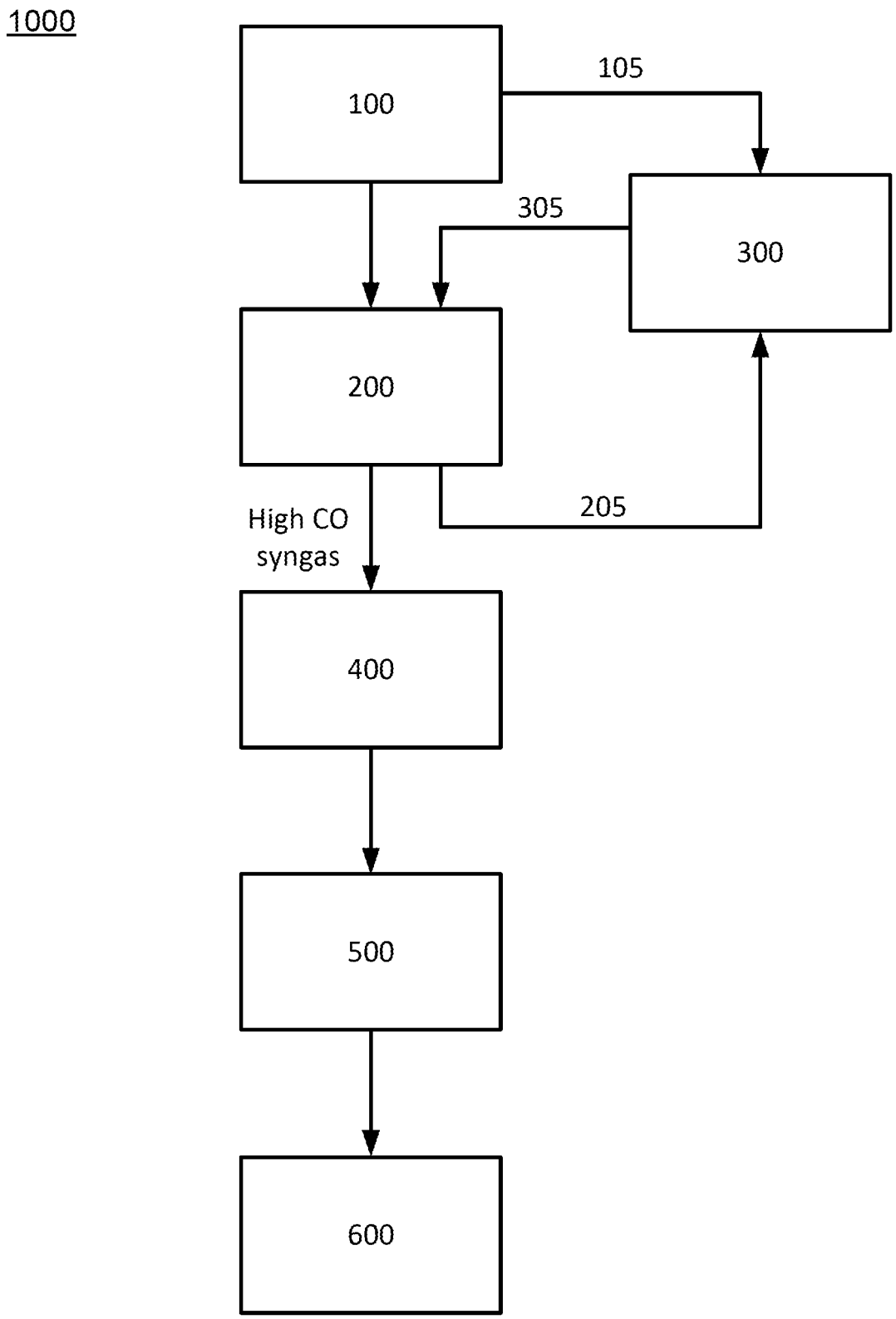
FIG. 2 is a schematic illustration of an embodiment of the invention in which carbon dioxide from a fuel cell unit's anode exhaust gas is supplied to a steam methane reformer to increase a carbon monoxide content of syngas and lower the hydrogen to carbon monoxide ratio of the syngas. In the embodiment of FIG. 2, natural gas from a pipeline is used as a feed gas for the steam methane reformer.

Referring to FIGS. 1A, 1B, and 2, various systems are described in which natural gas, organic waste, or biomass is converted to syngas that may in turn be used to produce liquid fuel. Although FIGS. 1A, 1B, and 2 describe methanol as an example of a liquid fuel synthesized by syngas produced in the SMR, the present application is not limited in this regard. One of ordinary skill in the art will appreciate that steam reforming syngas can also be used to produce hydrogen or other fuels, such as ethanol, propane, or even gasoline, and that other hydrocarbons may be used as fuel to the SMR.

Referring to FIG. 1A, a system 10A includes an SMR feed 100 comprised of natural gas from a pipeline. Referring to FIG. 1B, a system 10B includes an SMR feed 100 comprised of biogas, a mixture of $CO_2$, and $CH_4$. The only difference between the system 10A of FIG. 1A and the system 10B of FIG. 1B is the composition of the SMR feed 100. The SMR feed 100 comes from a hydrocarbon source, for example, a methane source which is low in $CO_2$ and produces a syngas with a higher than desired $H_2/CO$ ratio.

Referring to FIGS. 1A and 1B, the SMR feed 100 is fed to an SMR 200 to produce syngas according to formulas (1) and (2). Liquid fuel 400 is synthesized from the syngas produced in the SMR 200. Carbon dioxide in the syngas may be removed prior to feeding the syngas to the synthesis reactor. For example, the liquid fuel 400 may be methanol synthesized from the syngas produced in the SMR 200, according to formula (3). When the liquid fuel 400 is methanol, DME 500 can be synthesized by dehydration of the liquid fuel 400 according to formula (5). The DME 500 can be used in various applications 600, for example, applications related to agriculture, transportation or construction. In another example, the liquid fuel may be a Fischer Tropsch liquid.

When natural gas from a pipeline is used as the SMR feed 100 (see FIG. 1A), the carbon monoxide production is lower than desired (i.e., below the desired 2:1 ratio of hydrogen to carbon monoxide). Excess $H_2$ must be purified and exported separately or burned for fuel to optimize the yield from the synthesis reactor. In order to increase carbon monoxide production, some systems use biogas/anaerobic digester gas (ADG) as the SMR feed 100 (se FIG. 1B), as opposed to natural gas from a pipeline. For example, the ADG may have a 60/40 methane to carbon dioxide composition. However, the limited biogas availability limits the potential production sites.

Referring to FIG. 2, according to an exemplary embodiment, in order to increase a carbon monoxide content of the syngas produced by the SMR 200, a system 1000 includes a fuel cell unit 300. Similar to the system 10A of FIG. 1A, a portion of the SMR feed 100 of the system 1000 is comprised of natural gas from a pipeline, while the balance of the SMR feed is anode exhaust (comprising at least $CO_2$, CO, and $H_2$) from the fuel cell unit 300. Natural gas or other fuel 105 is fed to the fuel cell unit 300 to generate power and anode exhaust gas. A portion or all of the anode exhaust 305 from the fuel cell unit 300 is mixed with the feed 100 and fed to the SMR 200 (described in more detail below) to increase a carbon monoxide content of the syngas produced by the SMR 200. The anode exhaust 305 from the fuel cell unit 300 may be manipulated to optimize carbon monoxide in the gas stream to the SMR 200. In one embodiment, the water-gas shift reaction of formula (2) may be used to push the equilibrium toward the products to produce more carbon dioxide and hydrogen; as a result, carbon monoxide in the anode exhaust 305 may be minimized in the feed to the SMR 200. In one embodiment, the water-gas shift reaction of formula (2) may be used to push the equilibrium toward the reactants to produce more carbon monoxide; as a result, carbon monoxide in the anode exhaust 305 may be increased in the feed to the SMR 200.

Carbon monoxide of the anode exhaust 305 is mixed with feed 100 (for example, comprising natural gas) and the combination may be fed to SMR 200 as a single stream. To avoid fouling of processing equipment, the single stream enters the SMR 200 at processing conditions unfavorable to the formation of metal carbonyls, which are products of the reaction between the metal catalysts in the reformer and components of the stream entering SMR 200 (i.e. carbon monoxide). Thus, in one embodiment, SMR 200 is configured to operate at a temperature outside of the range of 30° C. to 250° C., at conventional pressures and concentrations for carbon monoxide. The thermodynamic equilibrium of the reaction leading to metal carbonyls at temperatures above about 250° C. strongly favors the reactants (i.e. the decomposition reaction), such that almost no metal carbonyls are formed in higher temperature ranges. Below about 30° C., the thermodynamic equilibrium of the reaction leading to metal carbonyls strongly favors the formation of the metal carbonyls, however, reaction kinetics dictate and almost no reaction occurs between the metal catalyst and feed stream. If metal carbonyls are formed during operation, they will deactivate the reforming catalyst and increase maintenance costs.

Figure 3:
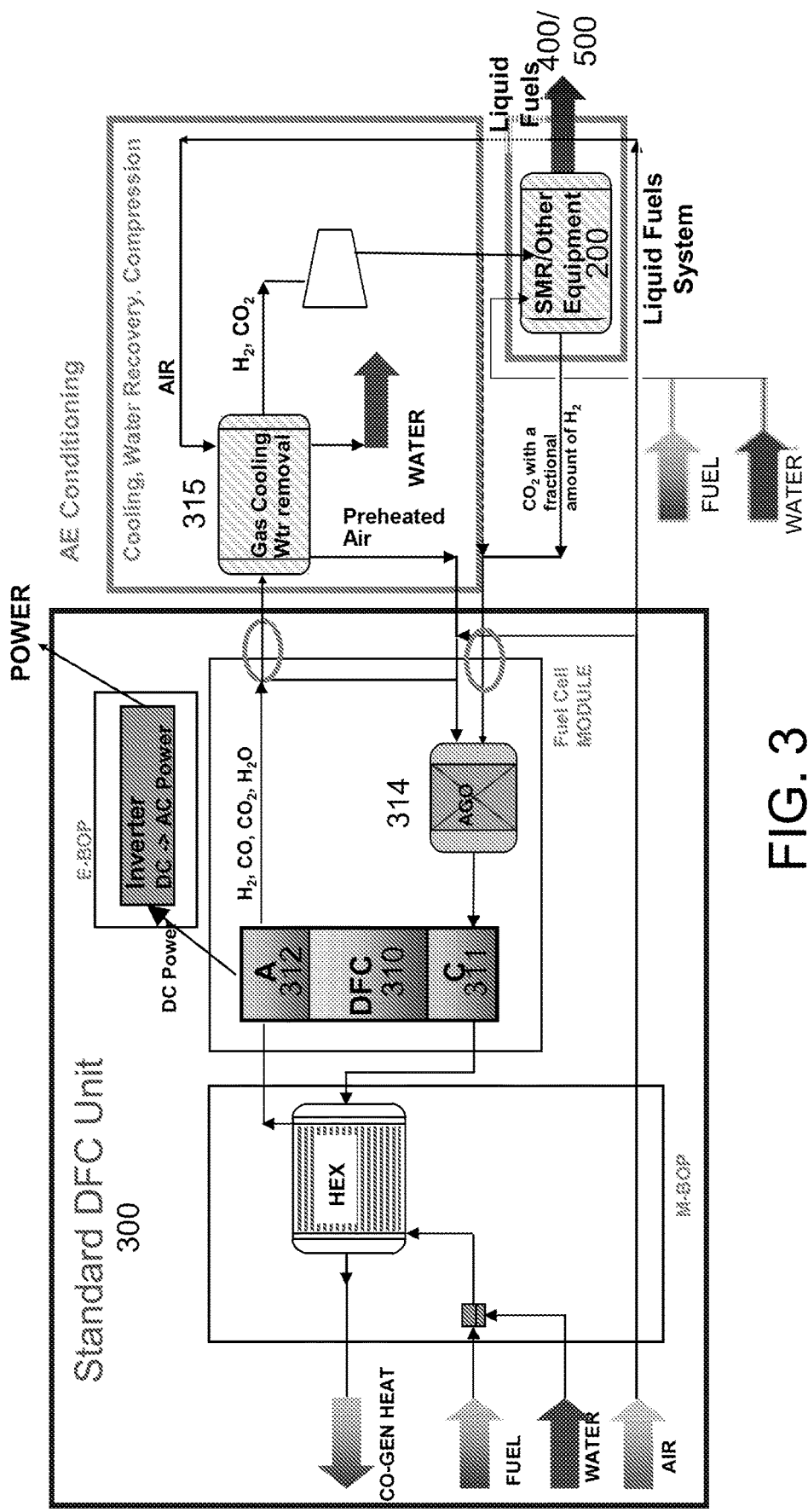
FIG. 3 illustrates the gas flow within the fuel cell unit of FIG. 2 and between the fuel cell unit and the steam methane reformer.

Compression of the anode exhaust gas may be needed as shown in FIG. 3, but is not shown in the simplified FIG. 2. When the fuel cell unit 300 includes a molten carbonate fuel cell, all or a portion 205 of the carbon dioxide produced by the SMR 200 may optionally be fed to the cathode of the fuel cell unit 300, either directly or most likely through an anode gas oxidizer, which converts any hydrocarbons in the gas to carbon dioxide and water (described in more detail below). Recycling carbon dioxide back to the cathode of the fuel cell unit 300 increases the output of carbon dioxide in the anode exhaust 305 fed to the SMR 200. As a result of the increased $CO_2$ input, a carbon monoxide content of the syngas produced by SMR 200 may also increase by at least a factor of two with better control of the $H_2$/CO ratio. Moreover, the production of hydrogen and carbon monoxide from SMR 200 may be up ten times the production of hydrogen and carbon monoxide from the fuel cell unit 300.

Liquid fuel 400 is synthesized from the syngas produced in the SMR 200 having a $H_2$/CO ratio of, for example, 2/1. For example, the liquid fuel 400 may be methanol synthesized from the syngas produced in the SMR 200, according to formula (3). When the liquid fuel 400 is methanol, DME 500 can be synthesized by dehydration of the liquid fuel 400 according to formula (5). The DME 500 can be used in various applications 600, for example, applications related to agriculture, transportation or construction. In another example, the liquid fuel may be a Fischer Tropsch liquid. Benefits of the system disclosed herein include a $H_2$/CO ratio of 2/1 for efficient production of liquid fuel, better control of the $H_2$/CO ratio by optimization of the anode exhaust feed to the SMR, increased syngas production (i.e. increased CO production), and highly efficient power production from the fuel cell unit.

In one aspect, anode exhaust gas from the fuel cell and the SMR produces syngas with a lower $H_2$/CO ratio than would be produced without the addition of anode exhaust gas to the SMR feed, and the syngas is converted to a liquid fuel(s). In one aspect, a combination of the hydrocarbon feed and the anode exhaust gas reduces a $H_2$/CO ratio of the syngas, as compared to a $H_2$/CO ratio of the syngas when the hydrocarbon feed is provided to the reformer without the anode exhaust gas. In one aspect, a combination of the natural gas feed and the anode exhaust gas reduces the $H_2$/CO ratio of the syngas, as compared to a $H_2$/CO ratio of the syngas when only the natural gas feed is provided to the steam methane reformer without the anode exhaust gas.

Although FIG. 2 illustrates an embodiment in which all or a portion 205 of the carbon dioxide produced by the SMR 200 is fed to the cathode of the fuel cell unit 300 (e.g., a molten carbonate fuel cell), the concepts described herein are not limited in this regard. In other embodiments, a portion 205 of the carbon dioxide produced by the SMR 200 may not be fed to the fuel cell unit 300. For example, in embodiments in which the fuel cell unit 300 does not include a molten carbonate fuel cell, the portion 205 of the carbon dioxide produced by the SMR 200 is not fed to the fuel cell unit 300.

Fluid flow through the fuel cell unit 300 and fluid communication between the fuel cell unit 300 and the SMR 200 will be described with reference to FIG. 3. As seen in FIG. 3, the fuel cell unit 300 includes a fuel cell 310 having a cathode 311 and an anode 312. The fuel cell 310 may be, for example, an internally reforming or a direct molten carbonate fuel cell ("MCFC") in which the fuel for the anode 312 is internally reformed in the fuel cell 310. However, an external reformer may also be employed in which case a reformer would be used to reform the fuel prior to delivery to the anode 312. The oxidant gas fed to the cathode 311, for example, by an anode gas oxidizer ("AGO") combustor 314 (described in detail below), is comprised of carbon dioxide, water vapor and air (nitrogen+oxygen).

In one embodiment, the anode exhaust from a MCFC is about 30% syngas ($H_2$+CO) and 70% $CO_2$. The syngas in the anode exhaust is added to the syngas produced by the SMR such that adding anode exhaust to the SMR feed increases the syngas production and overall efficiency of the system. For a MCFC to properly operate, $CO_2$ is added to the cathode side of the fuel cell during operation. In one embodiment, sufficient $CO_2$ is separated from the SMR outlet syngas and sent to the MCFC cathode, although other sources of $CO_2$, such as flue gas, could also be used. In one embodiment, the MCFC is configured to operate at a temperature of approximately 650° C.

As described above, the fuel cell 310 is a direct molten carbonate fuel cell, which operates at approximately 650° C. However, the concepts described herein are not limited in this regard. The fuel cell 310 may be any known type of fuel cell which has carbon dioxide in its anode exhaust, including other high temperature fuel cells. For example, the fuel cell 310 may be a solid oxide fuel cell (SOFC).

In one embodiment, the anode exhaust from a SOFC is about 50% syngas ($H_2$+CO) and 50% $CO_2$. The syngas in the anode exhaust is added to the syngas produced by the SMR such that adding anode exhaust to the SMR feed increases the syngas production and overall efficiency of the system. SOFC fuel cells do not require $CO_2$. In one embodiment, the SOFC is configured to operate at a temperature of approximately 800° C.

As described above, the fuel cell unit 300 shows a single representative fuel cell 310, but generally, fuel cell units contain many cells and the present invention is not limited in regard to having one cell. The fuel cell unit 300 may include a plurality of fuel cells 310 in the form of a fuel cell stack (not illustrated); where individual fuel cells 310 are stacked so that fuel and oxidizing gas/air are supplied to the anode and cathode sections, respectively, of the fuel cell stack. A plurality of fuel cell stacks may be arranged in series or in parallel.

The oxidant gas in the cathode 311 and the reformed hydrogen in the anode 312 undergo an electrochemical reaction in the fuel cell 310 to output power. This electrochemical reaction results in a substantial portion (approximately 65% to 85% or more) of the carbon dioxide in the oxidant gas being transferred from the cathode 311 to the anode 312 of the fuel cell 310. More particularly in a molten carbonate fuel cell, the carbon dioxide and oxygen react in the cathode 311 of the fuel cell 310 to produce carbonate ions which are then carried to the anode 312 of the fuel cell 310 through a fuel cell electrolyte. At the anode 312, the carbonate ions are reduced with hydrogen from the fuel to produce water and carbon dioxide. The net result is the above-mentioned transfer of a substantial portion of the carbon dioxide from the cathode 311 to the anode 312. Therefore, the molten carbonate anode exhaust gas predominantly contains carbon dioxide as well as unreacted hydrogen, carbon monoxide, water vapor and trace amounts of other gases.

If a high temperature solid oxide fuel cell is used to supply the anode exhaust gas, only oxygen ions are transferred and all of the carbon dioxide is from the carbon in the hydrocarbon feed gas. Thus, solid oxide anode exhaust is typically lower in carbon dioxide content, and more anode exhaust gas is required to provide the desired $H_2/CO$ ratio in the SMR outlet syngas.

The anode exhaust gas may be cooled and compressed in a compressor such that water in the gas condenses to liquid and is readily removed by a water separator. The compressor and the water separator are illustrated as a compressor/water separator unit 315 in FIG. 3. The removal of water increases the concentration of the carbon dioxide. At least a portion of the remaining anode exhaust gas 305, which is mostly comprised of hydrogen and carbon dioxide, is fed to the SMR 200. A pressure of the anode exhaust gas 305 is matched to a pressure of the SMR feed 100 flowing into the SMR 200.

According to the reverse water-gas shift reaction (see formula (2)), carbon monoxide is produced from the carbon dioxide and hydrogen, thereby increasing the carbon monoxide content of the syngas. In conventional systems, when natural gas from a pipeline is used as the SMR feed 100 (see FIG. 1A), the carbon monoxide production is lower than desired (i.e., below the desired 2:1 ratio of hydrogen to carbon monoxide). By increasing the carbon monoxide content of the syngas by feeding anode exhaust gas 305 to the SMR 200, a more desirable ratio of hydrogen to carbon monoxide may be attained. Thus, the amount of excess hydrogen in the syngas is reduced, and it is not necessary to include system components to remove excess hydrogen.

In one embodiment, the mixture of anode exhaust gas 305 and SMR feed gas 100 has a similar composition to ADG (which may have a 60/40 methane to carbon dioxide composition), and can therefore be used as a substitute for the biogas/ADG. While limited biogas availability limits the potential production sites, it is easier to find a location having the natural gas necessary to produced syngas in an SMR and power in the fuel cell, where the SMR syngas can be further processed to yield liquid fuel such as methanol, which can be further processed to yield DME.

As seen in FIGS. 2 and 3, when the fuel cell unit 300 includes a molten carbonate fuel cell 310, a portion 205 of the carbon dioxide (and a fractional amount of hydrogen) produced by the SMR 200 may optionally be fed to the cathode of the fuel cell unit 300, in particular, via the AGO combustor 314. Oxygen, for example, from preheated air output by the water separator unit 315, is also fed to the AGO combustor 314. The combustor AGO combustor 314 outputs at least nitrogen, oxygen, and carbon dioxide, which is fed to the cathode 311 of the fuel cell 310. Direct molten carbonate fuel cells are known to reduce NOx in the cathode gas by over 50% and potentially part or all of the hot exhaust gas from the SMR may be fed to the AGO to improve the heat recovery efficiency and reduce NOx emissions.

According to other exemplary embodiments, part or all of the cathode exhaust gas can be fed to the SMR 200 burner to replace part of the air going to the SMR burner. This allows the heat from the cathode exhaust be recovered in the SMR 200 and reduces the amount of fuel needed by the SMR 200. The lower oxygen content in the cathode exhaust gas may also reduce the NOx produced in the SMR burner. Integration of the SMR heat needs and fuel cell heat generation may be optimized.

The system 1000 of FIGS. 2 and 3 is a self-contained electrical power generation system. The fuel cell unit 300 can be sized to produce power equivalent to what the balance of plant (i.e., the SMR 200) needs. This makes this system 1000 ideal for stranded natural gas locations since the gas would be converted to methanol, DME or other high value liquid chemicals for easy transportation, and no outside electrical power would be required at the site. In other words, the fuel cell unit 300 provides low cost power to SMR 200, even if a grid is unavailable. This could have a major impact on gas to fuel economics for gas production in remote locations.

The fuel cell producing high $CO_2$ anode exhaust will also produce power which can be used by the SMR and FT production systems. Thus, stranded natural gas which is not near a pipeline or power grid can be converted to liquid fuels using power and anode exhaust from the fuel cell. The liquid fuels can then be transported by ships or trucks or other means.

Simulation Results

Figure 4:
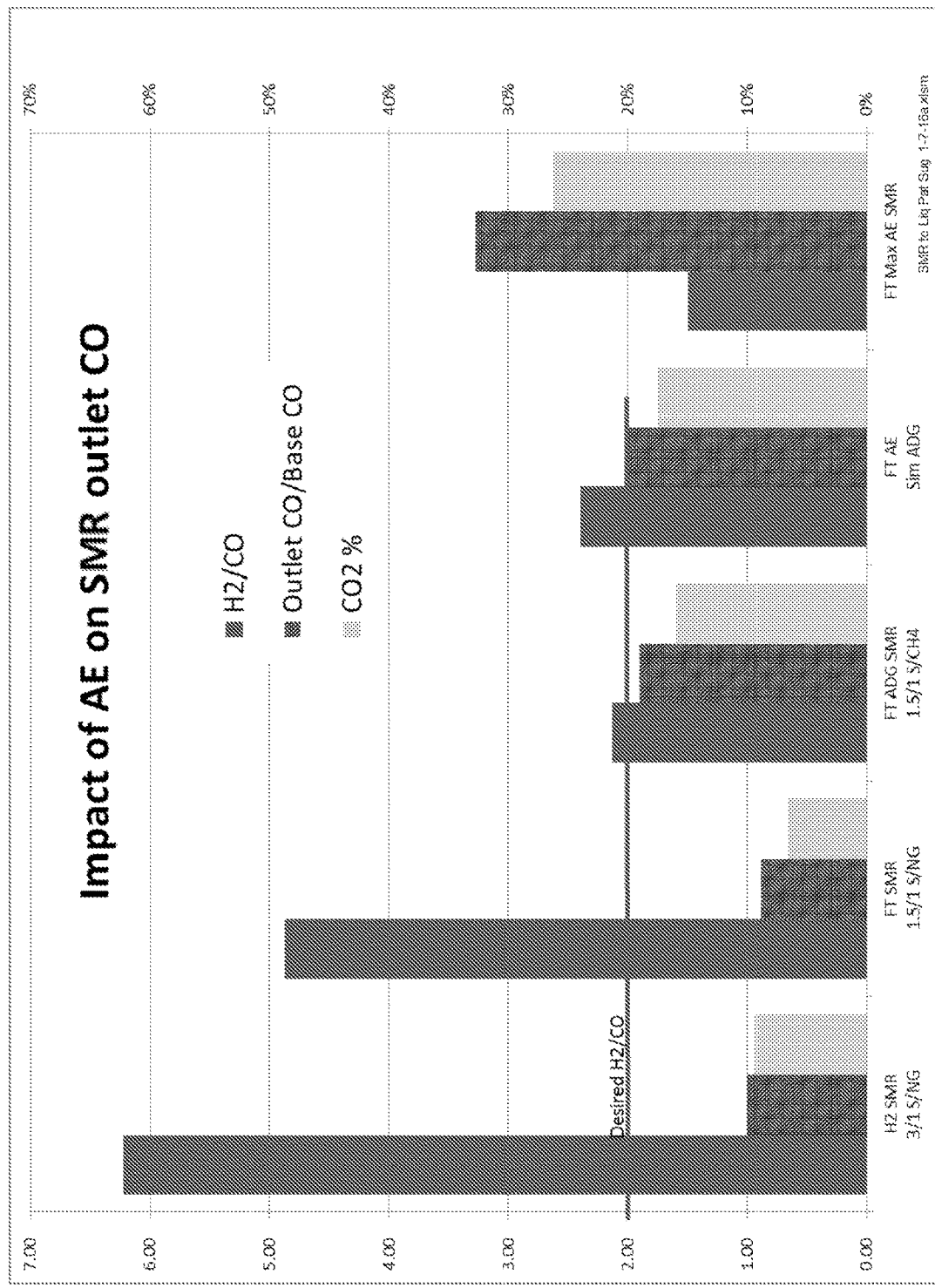
FIG. 4 is a graph summarizing simulation results of carbon monoxide production using various types and mixtures of feed gas.

Material balances for the steam methane reformer were estimated using CHEMCAD®. The results are summarized in the graph of FIG. 4, and described in detail in Tables 1-4 below. Table 1 shows syngas produced for high steam to natural gas (3:1 ratio) operation ("H2 SMR" in FIG. 4) for hydrogen production. Table 2 shows syngas produced for low steam to natural gas (1.5:1 ratio) operation ("FT SMR" in FIG. 4) for Fischer-Tropsch or other liquids production. Table 3 shows syngas produced when biogas/anaerobic digester gas is used as the SMR feed ("FT ADG SMR" in FIG. 4) for Fischer-Tropsch liquids production. Table 4 shows syngas produced when anode exhaust is mixed with a steam methane reformer natural gas feed ("FT AE SIM ADG" in FIG. 4) for Fischer-Tropsch liquids production. As seen in FIG. 4 and a comparison of Tables 1-4, carbon monoxide production is doubled when biogas/anaerobic digester gas is used as the SMR feed, and when anode exhaust is mixed with a steam methane reformer natural gas feed. Both the biogas/anaerobic digester gas feed and the anode exhaust plus natural gas feed increased the carbon monoxide production, reduced the excess hydrogen, and brought the hydrogen to carbon monoxide ratio closer to the desired ratio of 2:1 (as compared to the high steam to natural gas and low steam to natural gas operations). The anode exhaust plus natural gas feed produced slightly higher carbon monoxide amounts than the biogas/anaerobic digester gas. The anode exhaust plus natural gas feed could potentially produce even more carbon monoxide if the volume of anode exhaust was increased or optimized (see, for example, "FT MAX AE SMR" in FIG. 4).

The addition of anode exhaust to the natural gas feed also reduces the amount of natural gas feed required, since 5-15% of the syngas is provided by the anode exhaust. In addition, when the anode exhaust fuel supplied to the SMR is accounted for in the fuel cell operation, the power production efficiency increases to approximately 60% or more.

TABLE 1

SMR for H2 production 3/1 Stm/NG

| SMR to Liq Pat S | Stream No. | | | | |
|---|---|---|---|---|---|
| | 100 HC Feed | 300 Water to SMR | 3 Anode Exhaust to SMR | 601 Total Feed to SMR | 602 SMR Outlet |
| Molar flow lbmol/h | 100.00 | 300.00 | 0.00 | 400.00 | 537.01 |
| Mass flow lb/hr | 1,740.8 | 5,404.5 | 0.0 | 7,145.3 | 7,145.3 |
| Temp F. | 75° | 230° | 1129° | 572° | 1500° |
| Pres psia | 30.00 | 40.00 | 15.78 | 400.00 | 400.00 |
| IWCg | 830.38 | 1,107.17 | 436.87 | 11,071.68 | 11,071.68 |
| Enth MMBtu/hr | −3.376 | −36.061 | 0.000 | −32.960 | −22.582 |
| Vapor mole fraction | 75.000 | 230.000 | 1,129.000 | 572.000 | 1,500.000 |
| SCFM | 632.46 | 1,897.39 | 0.00 | 2,529.86 | 3,398.41 |
| Average mol wt | 17.41 | 18.02 | 34.84 | 17.86 | 13.31 |
| Actual dens lb/ft3 | 0.0012 | −0.2591 | 0.0000 | 0.0012 | 0.0002 |
| Actual vol ft3/min | 23808.58 | −347.67 | 2.03 | 101034.48 | 709124.58 |
| Cp Btu/lbmol-F. | 0.00/8.85 | 18.20/0.00 | 0.00/11.14 | 0.00/10.74 | 0.00/9.53 |
| Cp/Cv | 1.29711 Vap | Vap | 1.21711 Vap | 1.3102 Vap | 1.26664 Vap |
| Z factor | 0.9959 Vap | Vap | 1.0003 Vap | 0.9574 Vap | 1.0048 Vap |
| Visc cP | /0.01111 | 0.2524/ | /0.03679 | /0.02027 | /0.03886 |
| Th cond Btu/hr-ft-f | /0.0188 | 0.393/ | /0.0497 | /0.032 | /0.1253 |

| Components | lb·mole/hr | mole % | lb·mole/hr | mole % | lb·mole/hr | mole % | lb·mole/hr | mole % | lb·mole/hr | mole % |
|---|---|---|---|---|---|---|---|---|---|---|
| Hydrogen | 0.00 | 0.00 | 0.00 | 0.00 | 0.00 | 15.87 | 0.00 | 0.00 | 234.48 | 43.66 |
| Methane | 93.80 | 93.80 | 0.00 | 0.00 | 0.00 | 0.05 | 93.80 | 23.45 | 29.09 | 5.42 |
| Carbon Monoxide | 0.00 | 0.00 | 0.00 | 0.00 | 0.00 | 8.30 | 0.00 | 0.00 | 37.64 | 7.01 |
| Carbon Dioxide | 1.10 | 1.10 | 0.00 | 0.00 | 0.00 | 70.60 | 1.10 | 0.28 | 31.96 | 5.05 |
| Water | 0.00 | 0.00 | 300.00 | 100.00 | 0.00 | 3.88 | 300.00 | 75.00 | 200.63 | 37.38 |
| Nitrogen | 1.10 | 1.10 | 0.00 | 0.00 | 0.00 | 0.22 | 1.10 | 0.27 | 1.10 | 0.20 |
| Oxygen | 0.00 | 0.00 | 0.00 | 0.00 | 0.00 | 0.00 | 0.00 | 0.00 | 0.00 | 0.00 |
| Ethylene | 0.00 | 0.00 | 0.00 | 0.00 | 0.00 | 0.00 | 0.00 | 0.00 | 0.00 | 0.00 |
| Ethane | 1.90 | 1.00 | 0.00 | 0.00 | 0.00 | 0.00 | 1.90 | 0.47 | 0.00 | 0.00 |
| Propylene | 0.00 | 0.00 | 0.00 | 0.00 | 0.00 | 0.00 | 0.00 | 0.00 | 0.00 | 0.00 |
| Propane | 1.60 | 1.00 | 0.00 | 0.00 | 0.00 | 0.00 | 1.60 | 0.40 | 1.60 | 0.30 |
| Butylene | 0.00 | 0.00 | 0.00 | 0.00 | 0.00 | 0.00 | 0.00 | 0.00 | 0.00 | 0.00 |
| I-Butane | 0.00 | 0.00 | 0.00 | 0.00 | 0.00 | 0.00 | 0.00 | 0.00 | 0.00 | 0.00 |
| N-Butane | 0.50 | 0.60 | 0.00 | 0.00 | 0.00 | 0.00 | 0.50 | 0.12 | 0.50 | 0.09 |
| I-Pentane | 0.00 | 0.00 | 0.00 | 0.00 | 0.00 | 0.00 | 0.00 | 0.00 | 0.00 | 0.00 |
| N-Pentane | 0.00 | 0.00 | 0.00 | 0.00 | 0.00 | 0.00 | 0.00 | 0.00 | 0.00 | 0.00 |
| N-Hexane | 0.00 | 0.00 | 0.00 | 0.00 | 0.00 | 0.00 | 0.00 | 0.00 | 0.00 | 0.00 |
| Hydrogen Sulfide | 0.00 | 0.00 | 0.00 | 0.00 | 0.00 | 0.00 | 0.00 | 0.00 | 0.00 | 0.00 |
| Total | 100.00 | 100.00 | 300.00 | 100.00 | 0.00 | 99.01 | 400.00 | 100.00 | 537.01 | 100.00 |
| mmbtu/hr fuel | 35.52062 | | 0 | | 2.71E−08 | | 35.62063 | | 40.99652 | |
| Stm/C | | | 3.00 | | | | | | | |
| H2/CO | | | | | | | | | 6.23 | |
| CO m/h | | | | | | | | | 37.64 | 100.00% |

TABLE 2

SMR for Liquids production 1.5/1 Stm/NG
Stream No.

| SMR to Liq Pat S | 100<br>HC Feed | | 300<br>Water to SMR | | 3<br>Anode Exhaust to SMR | | 601<br>Total Feed to SMR | | 602<br>SMR Outlet | |
|---|---|---|---|---|---|---|---|---|---|---|
| Molar flow lbmol/h | 100.00 | | 150.00 | | 0.00 | | 250.00 | | 346.91 | |
| Mass flow lb/hr | 1,740.8 | | 2,702.3 | | 0.0 | | 4,443.1 | | 4,443.0 | |
| Temp F. | 75° | | 230° | | 1129° | | 572° | | 1500° | |
| Pres psia | 30.00 | | 40.00 | | 15.78 | | 400.00 | | 400.00 | |
| IWCg | 830.38 | | 1,107.17 | | 436.87 | | 11,071.68 | | 11.071.68 | |
| Enth MMBtu/hr | −3.376 | | −18.031 | | 0.000 | | −17.691 | | −10.527 | |
| Vapor mole fraction | 75.000 | | 230.000 | | 1,129.000 | | 572.000 | | 1,500.000 | |
| SCFM | 632.46 | | 948.70 | | 0.00 | | 1,581.16 | | 2,206.75 | |
| Average mol wt | 17.41 | | 18.02 | | 34.84 | | 17.77 | | 12.73 | |
| Actual dens lb/ft3 | 0.0012 | | −0.2591 | | 0.0000 | | 0.0012 | | 0.0002 | |
| Actual vol ft3/min | 23806.28 | | −173.64 | | 2.03 | | 63978.42 | | 461205.30 | |
| Cp Btu/lbmol-F. | 0.00/8.85 | | 18.20/0.00 | | 0.00/11.14 | | 0.00/10.95 | | 0.00/10.11 | |
| Cp/Cv | 1.29711 Vap | | Vap | | 1.21711 Vap | | 1.2751 Vap | | 1.24673 Vap | |
| Z factor | 0.9959 Vap | | Vap | | 1.0003 Vap | | 0.97 Vap | | 1.0058 Vap | |
| Visc cP | /0.01111 | | 0.2524/ | | /0.03679 | | /0.02001 | | /0.03696 | |
| Th cond Btu/hr-ft-f | /0.0188 | | 0.393/ | | /0.0497 | | /0.035 | | /0.1312 | |
| Components | lb·mole/hr | mole % | lb·mole/hr | mole % | lb·mole/hr | mole % | lb·mole/hr | mole % | lb·mole/hr | mole % |
| Hydrogen | 0.00 | 0.00 | 0.00 | 0.00 | 0.00 | 16.87 | 0.00 | 0.00 | 162.58 | 46.60 |
| Methane | 93.80 | 93.80 | 0.00 | 0.00 | 0.00 | 0.05 | 93.80 | 37.52 | 48.13 | 13.80 |
| Carbon Monoxide | 0.00 | 0.00 | 0.00 | 0.00 | 0.00 | 8.30 | 0.00 | 0.00 | 33.35 | 9.50 |
| Carbon Dioxide | 1.10 | 1.10 | 0.00 | 0.00 | 0.00 | 70.60 | 1.10 | 0.44 | 17.20 | 4.93 |
| Water | 0.00 | 0.00 | 150.00 | 100.00 | 0.00 | 3.08 | 150.00 | 60.00 | 84.44 | 24.20 |
| Nitrogen | 1.10 | 1.10 | 0.00 | 0.00 | 0.00 | 0.22 | 1.10 | 0.44 | 1.10 | 0.32 |
| Oxygen | 0.00 | 0.00 | 0.00 | 0.00 | 0.00 | 0.00 | 0.00 | 0.00 | 0.00 | 0.00 |
| Ethylene | 0.00 | 0.00 | 0.00 | 0.00 | 0.00 | 0.00 | 0.00 | 0.00 | 0.00 | 0.00 |
| Ethane | 1.90 | 1.90 | 0.00 | 0.00 | 0.00 | 0.00 | 1.90 | 0.76 | 0.00 | 0.00 |
| Propylene | 0.00 | 0.00 | 0.00 | 0.00 | 0.00 | 0.00 | 0.00 | 0.00 | 0.00 | 0.00 |
| Propane | 1.60 | 1.60 | 0.00 | 0.00 | 0.00 | 0.00 | 1.60 | 0.04 | 1.60 | 0.46 |
| Butylene | 0.00 | 0.00 | 0.00 | 0.00 | 0.00 | 0.00 | 0.00 | 0.00 | 0.00 | 0.00 |
| I-Butane | 0.00 | 0.00 | 0.00 | 0.00 | 0.00 | 0.00 | 0.00 | 0.00 | 0.00 | 0.00 |
| N-Butane | 0.50 | 0.50 | 0.00 | 0.00 | 0.00 | 0.00 | 0.50 | 0.20 | 0.50 | 0.14 |
| I-Pentane | 0.00 | 0.00 | 0.00 | 0.00 | 0.00 | 0.00 | 0.00 | 0.00 | 0.00 | 0.00 |
| N-Pentane | 0.00 | 0.00 | 0.00 | 0.00 | 0.00 | 0.00 | 0.00 | 0.00 | 0.00 | 0.00 |
| N-Hexane | 0.00 | 0.00 | 0.00 | 0.00 | 0.00 | 0.00 | 0.00 | 0.00 | 0.00 | 0.00 |
| Hydrogen Sulfide | 0.00 | 0.00 | 0.00 | 0.00 | 0.00 | 0.00 | 0.00 | 0.00 | 0.00 | 0.00 |
| Total | 100.00 | 100.00 | 150.00 | 100.00 | 0.00 | 99.01 | 250.00 | 100.00 | 348.91 | 100.00 |
| mmbtu/hr fuel | 35.52062 | | | | 2.71E−06 | | 35.52083 | | 39.56858 | |
| Stm/C | | | 1.50 | | | | | | | |
| H2/CO | | | | | | | | | 4.87 | |
| CO m/h | | | | | | | | | 33.35 | 88.60% |

TABLE 3

SMR for Liquids production 1.5/1 Stm/ADG CH4
Stream No.

| SMR to Liq Pat S | 100<br>HC Feed | 300<br>Water to SMR | 3<br>Anode Exhaust to SMR | 601<br>Total Feed to SMR | 602<br>SMR Outlet |
|---|---|---|---|---|---|
| Molar flow lbmol/h | 166.60 | 150.00 | 0.00 | 316.60 | 428.91 |
| Mass flow lb/hr | 4,536.5 | 2,702.3 | 0.0 | 7,238.7 | 7,238.7 |
| Temp F. | 75° | 230° | 1129° | 572° | 1500° |
| Pres psia | 30.00 | 40.00 | 15.78 | 400.00 | 400.00 |
| IWCg | 830.38 | 1,107.17 | 436.87 | 11,071.68 | 11,071.68 |
| Enth MMBtu/hr | −14.497 | −18.031 | 0.000 | −28.691 | −19.454 |
| Vapor mole fraction | 75.000 | 230.000 | 1,129.000 | 572.000 | 1,500.000 |
| SCFM | 1,053.69 | 948.70 | 0.00 | 2,002.38 | 2,712.73 |
| Average mol wt | 27.23 | 18.02 | 34.84 | 22.86 | 16.88 |
| Actual dens lb/ft3 | 0.0019 | −0.2591 | 0.0000 | 0.0015 | 0.0002 |
| Actual vol ft3/min | 39602.22 | −173.84 | 2.03 | 81617.58 | 567085.25 |
| Cp Btu/lbmol-F. | 0.00/8.73 | 18.20/0.00 | 0.00/11.14 | 0.00/10.75 | 0.00/9.98 |
| Cp/Cv | 1.305 Vap | Vap | 1.21711 Vap | 1.27086 Vap | 1.25123 Vap |
| Z factor | 0.9944 Vap | Vap | 1.0003 Vap | 0.9771 Vap | 1.006 Vap |
| Visc cP | /0.01334 | 0.2524/ | /0.03679 | /0.02231 | /0.03966 |
| Th cond Btu/hr-ft-f | /0.015 | 0.393/ | /0.0497 | /0.0322 | /0.1055 |

TABLE 3-continued

SMR for Liquids production 1.5/1 Stm/ADG CH4
Stream No.

| SMR to Liq Pat S | 100 HC Feed | | 300 Water to SMR | | 3 Anode Exhaust to SMR | | 601 Total Feed to SMR | | 602 SMR Outlet | |
|---|---|---|---|---|---|---|---|---|---|---|
| Components | lb·mole/hr | mole % | lb·mole/hr | mole % | lb·mole/hr | mole % | lb·mole/hr | mole % | lb·mole/hr | mole % |
| Hydrogen | 0.00 | 0.00 | 0.00 | 0.00 | 0.00 | 15.87 | 0.00 | 0.00 | 152.88 | 35.64 |
| Methane | 99.96 | 60.00 | 0.00 | 0.00 | 0.00 | 0.05 | 99.96 | 31.57 | 43.79 | 10.21 |
| Carbon Monoxide | 0.00 | 0.00 | 0.00 | 0.00 | 0.00 | 8.30 | 0.00 | 0.00 | 71.75 | 16.73 |
| Carbon Dioxide | 66.64 | 40.00 | 0.00 | 0.00 | 0.00 | 70.60 | 66.64 | 21.05 | 51.05 | 11.90 |
| Water | 0.00 | 0.00 | 150.00 | 100.00 | 0.00 | 3.98 | 150.00 | 47.38 | 109.44 | 25.51 |
| Nitrogen | 0.00 | 0.00 | 0.00 | 0.00 | 0.00 | 0.22 | 0.00 | 0.00 | 0.00 | 0.00 |
| Oxygen | 0.00 | 0.00 | 0.00 | 0.00 | 0.00 | 0.00 | 0.00 | 0.00 | 0.00 | 0.00 |
| Ethylene | 0.00 | 0.00 | 0.00 | 0.00 | 0.00 | 0.00 | 0.00 | 0.00 | 0.00 | 0.00 |
| Ethane | 0.00 | 0.00 | 0.00 | 0.00 | 0.00 | 0.00 | 0.00 | 0.00 | 0.00 | 0.00 |
| Propylene | 0.00 | 0.00 | 0.00 | 0.00 | 0.00 | 0.00 | 0.00 | 0.00 | 0.00 | 0.00 |
| Propane | 0.00 | 0.00 | 0.00 | 0.00 | 0.00 | 0.00 | 0.00 | 0.00 | 0.00 | 0.00 |
| Butylene | 0.00 | 0.00 | 0.00 | 0.00 | 0.00 | 0.00 | 0.00 | 0.00 | 0.00 | 0.00 |
| I-Butane | 0.00 | 0.00 | 0.00 | 0.00 | 0.00 | 0.00 | 0.00 | 0.00 | 0.00 | 0.00 |
| N-Butane | 0.00 | 0.00 | 0.00 | 0.00 | 0.00 | 0.00 | 0.00 | 0.00 | 0.00 | 0.00 |
| I-Pentane | 0.00 | 0.00 | 0.00 | 0.00 | 0.00 | 0.00 | 0.00 | 0.00 | 0.00 | 0.00 |
| N-Pentane | 0.00 | 0.00 | 0.00 | 0.00 | 0.00 | 0.00 | 0.00 | 0.00 | 0.00 | 0.00 |
| N-Hexane | 0.00 | 0.00 | 0.00 | 0.00 | 0.00 | 0.00 | 0.00 | 0.00 | 0.00 | 0.00 |
| Hydrogen Sulfide | 0.00 | 0.00 | 0.00 | 0.00 | 0.00 | 0.00 | 0.00 | 0.00 | 0.00 | 0.00 |
| Total | 166.60 | 100.00 | 150.00 | 100.00 | 0.00 | 99.01 | 316.60 | 100.00 | 428.91 | 100.00 |
| mmbtu/hr fuel | 34.50279 | | 0 | | 2.71E−06 | | 34.5028 | | 39.75952 | |
| Stm/C | | | 1.50 | | | | | | | |
| H2/CO | | | | | | | | | 2.13 | |
| CO m/h | | | | | | | | | 71.75 | 100.00% |

TABLE 4

SMR for Liquids production 2/1 STM/NG w AE to SMR
Stream No.

| SMR to Liq Pat S | 100 HC Feed | 300 Water to SMR | 3 Anode Exhaust to SMR | 601 Total Feed to SMR | 602 SMR Outlet |
|---|---|---|---|---|---|
| Molar flow lbmol/h | 100.00 | 200.00 | 100.00 | 400.00 | 518.04 |
| Mass flow lb/hr | 1,740.8 | 3,603.0 | 3,484.4 | 8,828.2 | 8,828.2 |
| Temp F. | 75° | 230° | 1129° | 572° | 1500° |
| Pres psia | 30.00 | 40.00 | 15.78 | 400.00 | 400.00 |
| IWCg | 830.38 | 1,107.17 | 436.87 | 11,071.68 | 11,071.68 |
| Enth MMBtu/hr | −3.376 | −24.041 | −11.829 | −35.322 | −25.204 |
| Vapor mole fraction | 75.000 | 230.000 | 1,129.000 | 572.000 | 1,500.000 |
| SCFM | 632.46 | 1,264.93 | 632.46 | 2,529.86 | 3,276.44 |
| Average mol wt | 17.41 | 18.02 | 34.64 | 22.07 | 17.04 |
| Actual dens lb/ft3 | 0.0012 | −0.2591 | 0.0000 | 0.0014 | 0.0002 |
| Actual vol ft3/min | 23806.28 | −231.78 | 2032793.47 | 103002.35 | 684723.25 |
| Cp Btu/lbmol-F. | 0.00/8.85 | 18.20/0.00 | 0.00/11.15 | 0.00/10.52 | 0.00/9.97 |
| Cp/Cv | 1.29711 Vap | Vap | 1.21711 Vap | 1.27984 Vap | 1.25192 Vap |
| Z factor | 0.9959 Vap | Vap | 1.0003 Vap | 0.976 Vap | 1.0057 Vap |
| Visc cP | /0.01111 | 0.2524/ | /0.03679 | /0.02233 | /0.03993 |
| Th cond Btu/hr-ft-f | /0.0188 | 0.393/ | /0.0497 | /0.0339 | /0.1045 |

| Components | lb·mole/hr | mole % | lb·mole/hr | mole % | lb·mole/hr | mole % | lb·mole/hr | mole % | lb·mole/hr | mole % |
|---|---|---|---|---|---|---|---|---|---|---|
| Hydrogen | 0.00 | 0.00 | 0.00 | 0.00 | 16.03 | 10.03 | 16.03 | 4.01 | 182.49 | 35.23 |
| Methane | 93.80 | 93.80 | 0.00 | 0.00 | 0.05 | 0.05 | 93.85 | 23.46 | 38.63 | 7.40 |
| Carbon Monoxide | 0.00 | 0.00 | 0.00 | 0.00 | 8.38 | 8.38 | 8.38 | 2.09 | 76.11 | 14.69 |
| Carbon Dioxide | 1.10 | 1.10 | 0.00 | 0.00 | 71.30 | 71.30 | 72.40 | 18.10 | 63.69 | 12.29 |
| Water | 0.00 | 0.00 | 200.00 | 100.00 | 4.02 | 4.02 | 204.02 | 51.00 | 153.71 | 29.67 |
| Nitrogen | 1.10 | 1.10 | 0.00 | 0.00 | 0.22 | 0.22 | 1.32 | 0.33 | 1.32 | 0.28 |
| Oxygen | 0.00 | 0.00 | 0.00 | 0.00 | 0.00 | 0.00 | 0.00 | 0.00 | 0.00 | 0.00 |
| Ethylene | 0.00 | 0.00 | 0.00 | 0.00 | 0.00 | 0.00 | 0.00 | 0.00 | 0.00 | 0.00 |
| Ethane | 1.90 | 1.90 | 0.00 | 0.00 | 0.00 | 0.00 | 1.90 | 0.48 | 0.00 | 0.00 |
| Propylene | 0.00 | 0.00 | 0.00 | 0.00 | 0.00 | 0.00 | 0.00 | 0.00 | 0.00 | 0.00 |
| Propane | 1.60 | 1.60 | 0.00 | 0.00 | 0.00 | 0.00 | 1.60 | 0.40 | 1.60 | 0.31 |
| Butylene | 0.00 | 0.00 | 0.00 | 0.00 | 0.00 | 0.00 | 0.00 | 0.00 | 0.00 | 0.00 |
| I-Butane | 0.00 | 0.00 | 0.00 | 0.00 | 0.00 | 0.00 | 0.00 | 0.00 | 0.00 | 0.00 |
| N-Butane | 0.50 | 0.50 | 0.00 | 0.00 | 0.00 | 0.00 | 0.50 | 0.13 | 0.50 | 0.10 |

TABLE 4-continued

SMR for Liquids production 2/1 STM/NG w AE to SMR

| SMR to Liq Pat S | 100 HC Feed | | 300 Water to SMR | | 3 Anode Exhaust to SMR | | 601 Total Feed to SMR | | 602 SMR Outlet | |
|---|---|---|---|---|---|---|---|---|---|---|
| Stream No. | | | | | | | | | | |
| I-Pentane | 0.00 | 0.00 | 0.00 | 0.00 | 0.00 | 0.00 | 0.00 | 0.00 | 0.00 | 0.00 |
| N-Pentane | 0.00 | 0.00 | 0.00 | 0.00 | 0.00 | 0.00 | 0.00 | 0.00 | 0.00 | 0.00 |
| N-Hexane | 0.00 | 0.00 | 0.00 | 0.00 | 0.00 | 0.00 | 0.00 | 0.00 | 0.00 | 0.00 |
| Hydrogen Sulfide | 0.00 | 0.00 | 0.00 | 0.00 | 0.00 | 0.00 | 0.00 | 0.00 | 0.00 | 0.00 |
| Total | 100.00 | 100.00 | 200.00 | 100.00 | 100.00 | 100.00 | 400.00 | 100.00 | 518.04 | 100.00 |
| mmbtu/hr fuel | 35.52062 | | | | 2.705989 | | 38.2266 | | 43.56224 | |
| Stm/C | | | 2.00 | 1.84 | | | | | | |
| H2/CO | | | | | | | | | 2.40 | |
| CO m/h | | | | | | | | | 76.11 | 202.18% |

The system 1000 increases the carbon monoxide content of syngas produced by a steam methane reformer by providing anode exhaust gas from a fuel cell to the steam methane reformer. Limited biogas availability and cost limit the potential production sites for biogas feeds. By increasing the carbon monoxide content of the syngas produced by the steam methane reformer, the system 1000 is able to substitute the biogas/ADG feed with a feed comprised of anode exhaust and natural gas, while achieving a similar hydrogen to carbon monoxide ratio, if not a better hydrogen to carbon monoxide ratio (i.e., closer to the desired 2:1 ratio). It is easier to find a location having a sufficient amount of natural gas necessary to produced syngas in an SMR and power in the fuel cell, where the syngas can be further processed to yield liquid fuel such as methanol, which can be further processed to yield DME or other useful chemicals. In the system 1000, the fuel cell also provides the power needed by process. This makes this system ideal for stranded natural gas locations since the syngas would be converted to methanol or DME or other high value liquid chemicals for easy transportation, and no outside electrical power would be required. Thus, more production sites may potentially be used for economically attractive chemicals production.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

References herein to the positions of elements (e.g., "top," "bottom," "above," "below," etc.) are merely used to describe the orientation of various elements in the Figures. It should be noted that the orientation of various elements may differ according to other exemplary embodiments, and that such variations are intended to be encompassed by the present disclosure.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A system for producing liquid fuel, comprising:
   a hydrocarbon source configured to provide a hydrocarbon feed that contains methane;
   a fuel cell unit configured to output anode exhaust gas containing $CO_2$; and
   a steam methane reformer configured to receive a first hydrocarbon feed portion from the hydrocarbon source and the anode exhaust gas from the fuel cell unit;
   wherein the steam methane reformer is configured to output a syngas having a first $H_2$/CO ratio of at most 2:1;
   wherein the fuel cell unit comprises a direct molten carbonate fuel cell (MCFC) configured to operate at a temperature in the range of 600° C. to 700° C.; and
   wherein the MCFC is configured to output anode exhaust gas comprising ($H_2$+CO) at an amount in the range of 20% to 40% and $CO_2$ at an amount in the range of 60% to 80%, wherein the syngas output from the steam methane reformer includes the ($H_2$+CO) of the anode exhaust gas, and wherein a cathode of the MCFC is configured to receive $CO_2$ from at least one of: $CO_2$ separated from the syngas, $CO_2$ output by an anode gas oxidizer combustor, or a $CO_2$-containing flue gas.

2. The system according to claim 1, wherein the hydrocarbon source is a natural gas source or a biogas source.

3. The system according to claim 1, wherein the steam methane reformer is configured to operate at a temperature outside of the range of 30° C. to 250° C.

4. The system according to claim 1, wherein an anode of the fuel cell unit is configured to receive a second hydrocarbon feed portion from the hydrocarbon source.

5. The system according to claim 4, wherein the fuel cell unit is further configured to receive a first portion of $CO_2$ output by the steam methane reformer.

6. The system according to claim 5, further comprising an anode gas oxidizer combustor configured to receive a second portion of $CO_2$ output by the steam methane reformer, wherein a cathode of the fuel cell unit is configured to receive $CO_2$ output by the anode gas oxidizer combustor.

7. The system according to claim 1, further comprising a liquid fuel producer configured to convert the syngas to the liquid fuel, wherein the liquid fuel comprises at least one of methanol or a Fischer-Tropsch liquid.

8. The system according to claim 1, wherein the liquid fuel is methanol, wherein the hydrocarbon source is a natural gas source, and wherein the steam methane reformer is configured to receive a natural gas feed from the natural gas source.

9. The system according to claim 8, wherein the steam methane reformer is configured to operate at a temperature outside of the range of 30° C. to 250° C.

10. The system according to claim 1, wherein the anode exhaust gas is added to the first hydrocarbon feed portion such that the steam methane reformer is configured to receive the first hydrocarbon feed portion and the anode exhaust gas as a single stream.

11. A system for producing liquid fuel, comprising:
a hydrocarbon source configured to provide a hydrocarbon feed that contains methane;
a fuel cell unit configured to output anode exhaust gas containing $CO_2$; and
a steam methane reformer configured to receive a first hydrocarbon feed portion from the hydrocarbon source and the anode exhaust gas from the fuel cell unit;
wherein the steam methane reformer is configured to output a syngas having a first $H_2$/CO ratio of at most 2:1;
wherein the fuel cell unit comprises a solid oxide fuel cell (SOFC) configured to operate at a temperature in the range of 800° C. to 1000° C.; and
where the SOFC is configured to output anode exhaust gas comprising ($H_2$+CO) at an amount in the range of 40% to 60% and $CO_2$ at an amount in the range of 40% to 60%, wherein the syngas output from the steam methane reformer includes the ($H_2$+CO) of the anode exhaust gas, and wherein the steam methane reformer is further configured to receive recycled $CO_2$ separated from the syngas.

12. A self-contained electrical power generation system comprising:
a fuel cell unit comprising:
an anode configured to receive a first hydrocarbon feed portion from a hydrocarbon source and output an anode exhaust gas comprising $CO_2$; and
a cathode;
a steam methane reformer configured to receive a second hydrocarbon feed portion from the hydrocarbon source and the anode exhaust gas; and a compressor configured to receive the anode exhaust gas from the anode and output the anode exhaust to the steam methane reformer; wherein the compressor is configured to separate water from the anode exhaust gas;
wherein the steam methane reformer is configured to output a syngas.

13. The system according to claim 12, wherein the fuel cell unit is configured to supply power to the steam methane reformer.

14. The system according to claim 12, wherein the cathode is configured to receive carbon dioxide from the steam methane reformer.

15. The system according to claim 14, further comprising an anode gas oxidizer ("AGO") combustor configured to receive the carbon dioxide from the steam methane reformer and output at least nitrogen, oxygen, and carbon dioxide to the cathode.

16. The system according to claim 15, further comprising a compressor configured to receive the anode exhaust gas from the anode and output the anode exhaust to the steam methane reformer; wherein the compressor is configured to output air to the AGO combustor.

17. A self-contained electrical power generation system comprising:
a fuel cell unit comprising:
an anode configured to receive a first hydrocarbon feed portion from a hydrocarbon source and output an anode exhaust gas comprising $CO_2$; and
a cathode;
a steam methane reformer configured to receive a second hydrocarbon feed portion from the hydrocarbon source and the anode exhaust gas;
wherein the steam methane reformer is configured to output a syngas; and
wherein the cathode is configured to receive carbon dioxide from the steam methane reformer.

18. The system according to claim 17, wherein the fuel cell unit is configured to supply power to the steam methane reformer.

19. The system according to claim 18, further comprising an anode gas oxidizer ("AGO") combustor configured to receive the carbon dioxide from the steam methane reformer and output at least nitrogen, oxygen, and carbon dioxide to the cathode.

20. The system according to claim 17, further comprising a compressor configured to receive the anode exhaust gas from the anode and output the anode exhaust to the steam methane reformer; wherein the compressor is configured to output air to the AGO combustor.

* * * * *